under 35 U.S.C. 154(b) by 91 days.

(12) United States Patent
Beran (10) Patent No.: US 9,358,368 B2
(45) Date of Patent: *Jun. 7, 2016

(54) CATHETER SECUREMENT DEVICE (71) Applicant: CareFusion 303, Inc., San Diego, CA (US)

(72) Inventor: Anthony V. Beran, Santa Ana, CA (US)

(73) Assignee: CareFusion 303, Inc., San Diego, CA (US)

( * ) Notice: Subject to any disclaimer, the term of this patent is extended or adjusted under 35 U.S.C. 154(b) by 91 days.

This patent is subject to a terminal disclaimer.

(21) Appl. No.: 14/286,851

(22) Filed: May 23, 2014

(65) Prior Publication Data

US 2014/0276543 A1    Sep. 18, 2014

Related U.S. Application Data (60) Division of application No. 13/015,495, filed on Jan. 27, 2011, now Pat. No. 8,734,401, which is a continuation of application No. 11/590,535, filed on Oct. 31, 2006, now Pat. No. 7,922,697.

(51) Int. Cl.
*A61M 25/02*    (2006.01)

(52) U.S. Cl.
CPC ....... *A61M 25/02* (2013.01); *A61M 2025/0246* (2013.01); *A61M 2025/0266* (2013.01); *A61M 2025/0293* (2013.01)

(58) Field of Classification Search
CPC ...................... A61M 2025/0266; A61M 25/02
See application file for complete search history.

(56) References Cited

U.S. PATENT DOCUMENTS

| 1,987,137 | A | 1/1935 | Walters |
|---|---|---|---|
| 2,908,269 | A | 10/1959 | Cheng |
| 4,170,995 | A | 10/1979 | Levin |
| 4,360,025 | A | 11/1982 | Edwards |
| 5,192,274 | A | 3/1993 | Bierman |
| 5,263,939 | A | 11/1993 | Wortrich |
| D375,355 | S | 11/1996 | Bierman |
| 5,693,032 | A | 12/1997 | Bierman |
| 6,428,516 | B1 | 8/2002 | Bierman |
| 6,491,664 | B2 | 12/2002 | Bierman |
| 6,582,403 | B1 | 6/2003 | Bierman |
| 6,827,705 | B2 | 12/2004 | Bierman |
| 6,901,287 | B2 | 5/2005 | Davis |
| 7,988,674 | B2 | 8/2011 | Adams |
| 2002/0068904 | A1 | 6/2002 | Bierman |
| 2005/0192540 | A1 | 9/2005 | Kessler |

(Continued)

OTHER PUBLICATIONS

International Search Report and Written Opinion issued for PCT/US2007/022964; Dated: Apr. 7, 2008; 12 pages.

*Primary Examiner* — Imani Hayman
(74) *Attorney, Agent, or Firm* — McDermott Will & Emery LLP (57) ABSTRACT

A device for securing a medical implement, such as a catheter to a body of a patient. The device having an adhesive pad for securing the pad to the body of a patient. An adjustable plate is rotatable with respect to the fixed plate to secure a catheter. In some aspects, a pair of adjustable plates can be rotated with respect to the fixed plate. Tabs affixed to the fixed plate and the adjustable plate cooperate with each other to secure a catheter there between. The adjustable plate can be rotated so as to retain a catheter between the tabs. Complementary pawl and ratchet members are used to enable limited rotation of the plates with respect to one another and to fix the plates in a selected adjustment position.

11 Claims, 5 Drawing Sheets

(56) References Cited

U.S. PATENT DOCUMENTS

2005/0273058 A1    12/2005   Bierman
2006/0058738 A1     3/2006   Ponzi
2006/0135944 A1     6/2006   Bierman

CATHETER SECUREMENT DEVICE

CROSS REFERENCE TO RELATED APPLICATIONS

The present application is a divisional application of U.S. application Ser. No. 13/015,495, filed Jan. 27, 2011, now U.S. Pat. No. 8,734,401 which is a continuation application of U.S. application Ser. No. 11/590,535, filed Oct. 31, 2006, now U.S. Pat. No. 7,922,697, the entire contents of which are incorporated by reference herein for all purposes.

BACKGROUND OF THE INVENTION

1. Field of the Invention

The present invention pertains to a securement device for securing a medical implement to the body of a patient, and, more particularly, to securement devices for fixing various catheters to the body of a patient.

2. Description of the Prior Art

Previously, it was known to affix a medical implement, such as a catheter, to the body of a patient in order to introduce fluids and medications directly into the patient or to withdraw fluids, for example, blood, from the patient. The tip of an intravenous or IV catheter is usually positioned into a larger vein close to the patient's heart or into the right atrium. If the catheter is inserted through a large neck or chest vein, it is referred to as a central venous catheter or CVC. A venous catheter peripherally inserted into the heart through a vein in the arm is referred to as a peripherally inserted central catheter or PICC. Often the catheter may remain in place for days. The healthcare worker affixed the catheter to the patient using long pieces of tape. This was undesirable since tape often collects dirt and other contaminants and it was necessary to change the tape periodically, usually daily.

Various catheter securement devices have been developed to obviate the need for frequent application of tape to the body of a patient. One such securement device included a flexible clamp with winged extensions that would be sutured to the patient.

Other catheter securement devices provided an adhesive layer between the flexible clamp and the patient's skin. See for example, U.S. Pat. No. 5,192,274. The securement device included a base with adhesive on one side and spaced-apart pins protruding from the other side. The pins were adapted to be engaged in spaced-apart holes in a catheter, for example, a triple lumen catheter. To affix the catheter to the securement device it was necessary to press downwardly against the patient, which could produce discomfort and possible pain.

More recently, a catheter anchoring system is disclosed in U.S. Pat. Nos. 6,582,403 and 6,770,055 which is secured to a patient's skin without the use of tape, needles or suturing. The anchoring system includes a base connected to a cover assembly by way of flexible hinges. The base is attached to an anchor pad that has an adhesive bottom surface for attachment to the skin of a patient. A channel is formed between posts in the base that can be moved linearly toward and away from one another. A catheter can be retained within the channel. At least one post is movable from the other so as to vary the distance between the posts and accommodate different sizes of catheters and catheter fittings. The catheter anchoring system of U.S. Pat. Nos. 6,582,403 and 6,770,055 is limited in operation because of the restricted linear movement of the posts with respect to one another and the hinged cover assembly. Thus, there remains the need for an improved universal type catheter securement device that more easily accommodates a variety of types and sizes of catheters.

SUMMARY OF THE INVENTION

The present invention provides an improved securement device for securing a medical implement to the body of a patient. The securement device includes a pad or base having a top surface and a bottom surface. At least a portion of the bottom surface of the pad has adhesive thereon for securing the securement device to the body of a patient. Complementary members are secured to the top surface of the pad or base. The complementary members are rotationally adjusted with respect to one another to secure a medical implement therebetween.

In one embodiment, the complementary members include a fixed plate secured to the top surface of the pad and an adjustable plate pivotally secured to the pad for rotational movement relative to the fixed plate. Retention means can be provided on the complementary members to enhance gripping or securing of the catheter in place between the complementary members. The retention means can be a bracket on one complementary member and a tab on the other complementary member. Alternately, the retention means could be a post on each of the complementary members. In another alternative, the surfaces of the complementary members that are adapted to engage the medical implement are textured to enhance engagement with the medical implement. Further, if desired, the rotational movement of the adjustable plate can be restricted by use of a cooperating ratchet and pawl on the fixed plate and the adjustable plate, respectively.

In a further embodiment of the present invention, a pair of adjustable members are pivotally secured to a fixed member for relative movement with respect to one another. The adjustable members may be plates or arms rotatable on separate pivots or on a common pivot. Retention means in the form of posts are affixed to the adjustable members and extend outwardly therefrom. Rotation of the adjustable members will change the spacing between the posts and enable the posts to secure winged catheters having different spacings between the openings in the wings, as well as to secure catheters of different sizes and shapes. Complementary pawl and ratchet teeth can be used to permit adjustment of the arms or plates with respect to one another and to retain the arms or plates in a selected adjusted position.

The present invention provides an improved securement device for affixing a medical implement to the body of a patient, with a minimum of discomfort to the patient.

The present invention also provides an improved securement device for affixing a medical implement to the body of a patient, which can readily accommodate a variety of different sizes and shapes of medical implements.

Other advantages of the present invention will become more apparent from the following detailed description of preferred embodiments.

BRIEF DESCRIPTION OF THE DRAWING

There is shown in the attached drawing presently preferred embodiments of the present invention, wherein like numerals in the respective views refer to like elements and wherein.

DETAILED DESCRIPTION OF THE PREFERRED EMBODIMENTS OF THE PRESENT INVENTION

Figure 1:
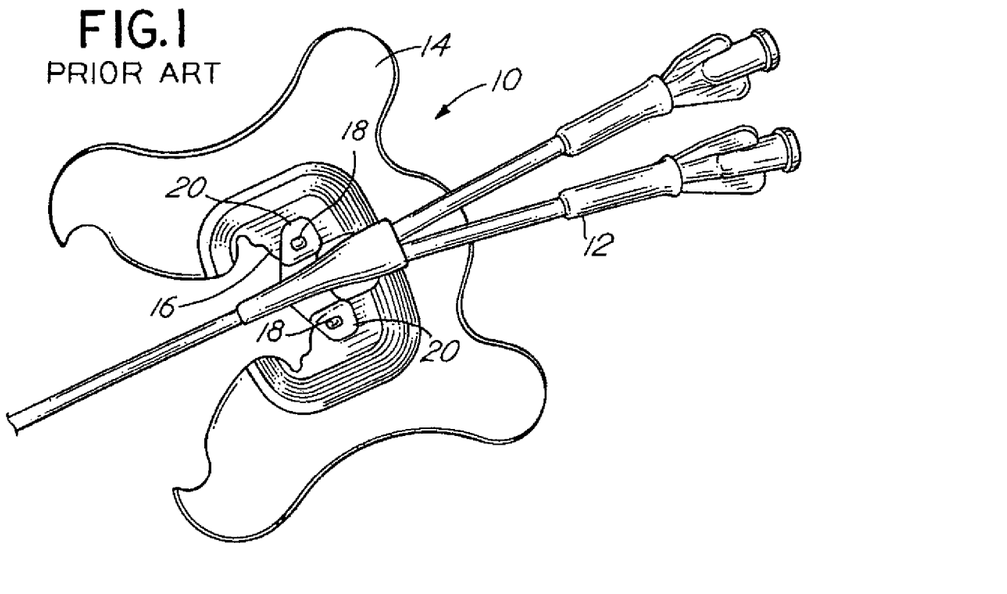
FIG. 1 illustrates a prior art winged catheter that is engaged with a base affixed to the body of the user, wherein the winged catheter is secured to posts fixed on the base.

Referring to FIG. 1, there is shown a prior art device for securing peripherally-inserted central catheters (PICC) in place on a patient. The device 10 for securing the catheter 12 in place includes a base 14 adapted to be secured to the skin of a patient by an adhesive. Affixed to the base 14 is an adapter 16 having a pair of posts 18 extending upwardly therefrom. The posts 18 engage in openings in the wings 20 of the catheter 12 for securing the catheter 12 in place on the device 10. A separate adapter is needed for a specific catheter and the usefulness of the device is therefor limited.

Figure 2:
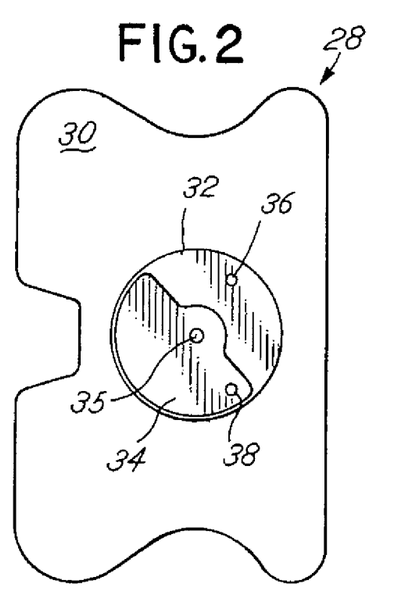
FIG. 2 shows an adjustable catheter securement device having plates rotationally adjustable with respect to one another.
Figure 3:
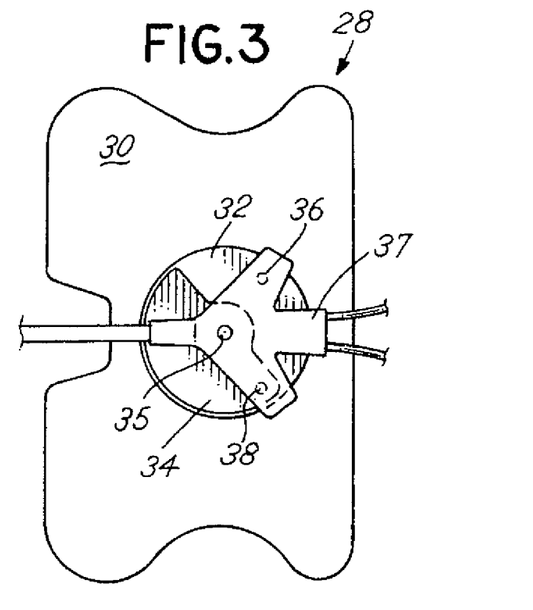
FIG. 3 shows the adjustable catheter securement device of FIG. 2, with a winged catheter retained thereon.

With reference to FIGS. 2 and 3, there is disclosed a securement device 28 that can be used more universally to secure winged catheters with different spacings between the openings in the wings of the catheter. The securement device 28 includes a base or pad means 30 having adhesive on at least a portion of one surface (the surface adapted to face and engage the patient) and a fixed member or plate 32 secured on the opposite surface (the surface facing away from the patient. Rotationally secured to the base 30 by the pivot pin 35 is an adjustable plate 34. The fixed member 32 has a projection in the form of a pin or post 36 extending upwardly and generally perpendicularly with respect to the fixed member 32. The adjustable plate 34 has a projection in the form of a pin or post 38 extending upwardly and generally perpendicularly with respect to the adjustable plate 34. The adjustable plate 34 is generally planar and parallel to the generally planar fixed plate 32. When the adjustable plate 34 is rotated with respect to the fixed plate 32 about the axis of the pivot pin 35, the spacing between the posts 36, 38 is varied, whereby the securement device 28 can be adapted readily to accommodate a winged catheter 37. Catheters with different spacings between the openings therein can be readily accommodated. Further, it will be understood by persons skilled in the art that the posts can be secured as desired to the fixed member and the adjustable plate. For example, post 38 can be positioned outwardly or inwardly on the adjustable plate 34 from the position illustrated in the drawing. The shape of the posts can be altered as needed. They can be cylindrical, with a textured outer surface. The posts may have a bullet shape at the top, or another form, such as a pyramid or a cone or Christmas tree ball structure.

The fixed member 32 and post 36 may be considered to be a first complementary securement means and the adjustable plate 34 and the post 38 may be considered to be a second complementary securement means. The two complementary securement means are constructed and arranged to be rotationally adjusted with respect to one another to secure a medical implement, such as a catheter. The posts 36 and 38 may be considered to be retention means on the respective first and second complementary means for engaging with and retaining the catheter.

Figure 4:
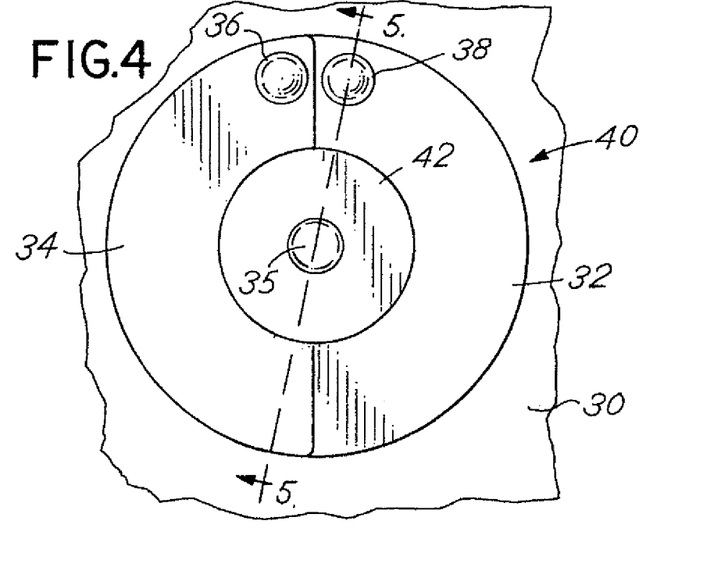
FIG. 4 shows a second embodiment of an adjustable catheter securement device embodying principles of the present invention.
Figure 5:
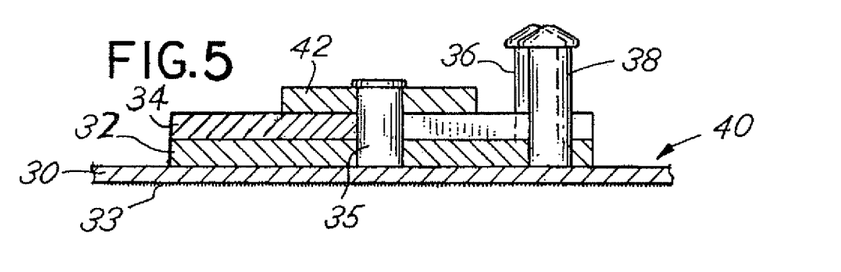
FIG. 5 shows a cross sectional view through the adjustable catheter securement device of FIG. 4, taken generally along the line 5-5 of FIG. 4.

Turning to FIGS. 4 and 5 there is shown a modified securement device 40 similar to the securement device 28 of FIGS. 2 and 3, but wherein the pivot pin 35 is secured at one end to the fixed plate 32 and at the other end to a cover or stabilizing plate 42. The fixed plate 32 is suitably bonded or joined to the base 30, which is fabricated from a flexible material, such as a cotton or plastic fiber material having an adhesive 33 for affixation of the securement device 40 the skin of a patient. The operation of the securement device 40 is essentially the same as that for the securement device 28 described above.

It will be observed that the radial position of the posts 36, 38 from the axis of the pivot pin 35 can be adjusted as desired to accommodate different sizes of catheters therebetween and to adjust the necessary rotational movement of the rotary adjustable plate 34. For example, to accommodate small diameter catheters, the posts 36, 38 could be moved radially inwardly toward the axis of pivot pin 35. With relatively small rotational movement of the adjustable plate 34 with respect to the fixed plate 32, the catheter could be firmly held. On the other hand, to accommodate relatively large diameter catheters, the posts 36, 38 could be moved radially outwardly from the axis of pivot pin 35.

Figure 6:
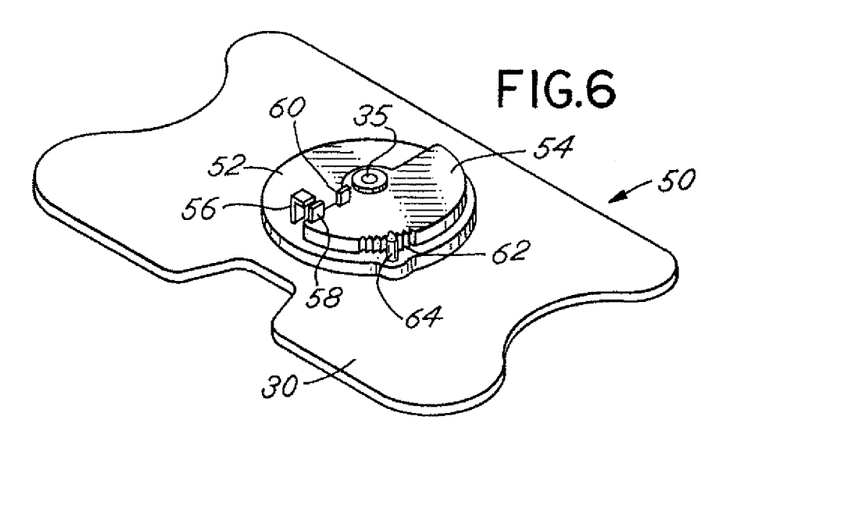
FIG. 6 shows a third embodiment of an adjustable catheter securement device embodying principles of the present invention.
Figure 7:
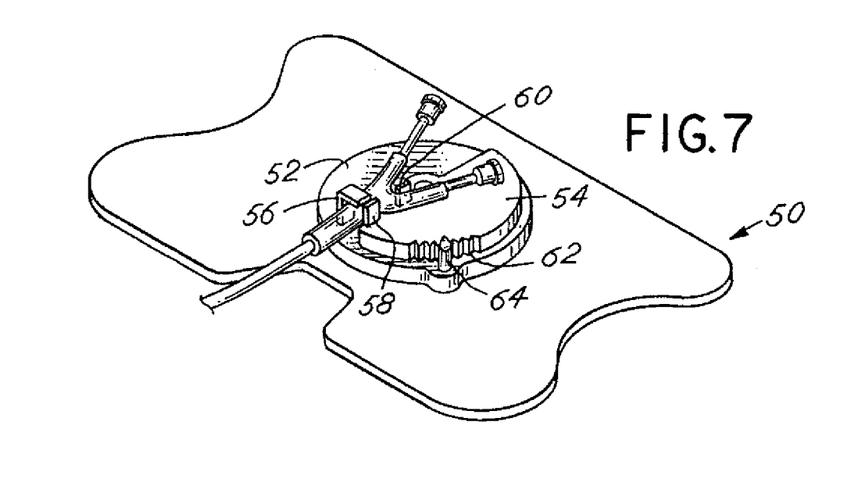
FIG. 7 shows a catheter retained on the adjustable catheter securement device of FIG. 6.

In FIG. 6 there is shown a third embodiment of the present invention, wherein the securement device 50 includes a base 30 having adhesive on at least a portion of the surface to be adhered to the skin of a patient, a fixed plate 52 on the base 30 and an adjustable plate 54 rotationally mounted on the base for rotation about pivot pin 35. This securement device is suitable for two Luer locks, split or offset and for StatLock® PICCII, VCV2 devices, and urinary catheters. Rather than utilizing posts as the retention means, in the third embodiment the retention means comprises an angle bracket 56 secured to the fixed plate 52 and a tab or projection 58 secured to the adjustable plate 54 and extending upwardly therefrom. The angle bracket 56 and the tab 58 are adapted to cooperate to secure the body of a catheter therebetween. Different diameter catheters can readily be held by the bracket 56 and the tab 58. For some applications an additional tab 60 can be secured to the adjustable plate 54. A Y-shaped catheter can be securely stabilized on the securement device 50 by positioning the juncture of the Y of the catheter against the tab 60 and rotating the adjustable plate 54 with respect to the fixed plate 52 to securely hold the catheter between the bracket 56 and the tab 58. See FIG. 7.

In order to help fix the adjustable plate 54 with respect to the fixed plate 52 in use, ratchet teeth 62 may be provided on the adjustable plate 54 and a pawl 64 may be provided on the fixed plate 52. It will be understood that the fixed plate 52 and the adjustable plate 54 may be fabricated from a suitable material, such as metal or plastic, that will have some resiliency or give. Preferably, the fixed plate 52 and the adjustable plate 54 are molded from a suitable plastic, such as polypropylene, nylon, polycarbonate or acrylonitrile butadiene styrene (ABS). Thus, the pawl 64 is constructed and arranged to have limited movement with respect to the ratchet teeth 62. When the pawl 64 is released from between a pair of adjacent ratchet teeth 62, the adjustable plate 54 can be rotated with respect to the fixed plate 52. When the pawl 64 is engaged between a selected pair of adjacent ratchet teeth 62, the position of the adjustable plate 54 is fixed with respect to the fixed plate 52. The pawl 64 cooperates with the ratchet teeth 62 to resist rotational movement of the adjustable plate 54 with respect to the fixed plate 52.

Figure 8:
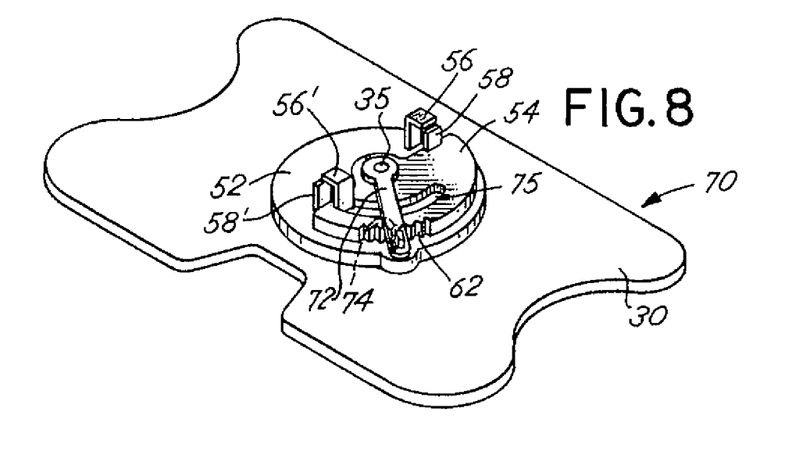
FIG. 8 shows a fifth embodiment of an adjustable catheter securement device embodying principles of the present invention.

In FIG. 8 there is shown a further embodiment similar to that of FIG. 6, but having two spaced apart retention means, rather than one, and having a pawl on an arm member. The securement device 70 includes a base 30 having adhesive on at least a portion of the surface to be adhered to the skin of a patient, a fixed plate 52 on the base 30 and an adjustable plate 54 rotationally mounted on the base for rotation about pivot pin 35. Rather than utilizing a single bracket/tab retention means, as in the embodiment of FIG. 6, in the embodiment of FIG. 7, the retention means comprises two pairs of cooperating brackets and tabs. An angle bracket 56 secured to the fixed plate 52 cooperates with a tab or projection 58 secured to the adjustable plate 54 and extending upwardly therefrom. The angle bracket 56 and the tab 58 are adapted to cooperate to secure the body of a catheter there between. Similarly, the angle bracket 56' is secured at one end to the fixed plate 52 and extends through the window or slotted opening 75 in the adjustable plate 54 for cooperating with a tab 58' on the adjustable plate 54. The two retention means are spaced apart on opposite sides of the axis of pivot 35 so as to engage with spaced portions on a catheter for retaining same. Different diameter catheters can readily be held by the first retention means (bracket 56 and the tab 58) and the second retention means (bracket 56' and tab 58'). It will be understood by persons skilled in the art that the brackets 56, 56' may have straight sides as shown, or that the sides can be curved to better adapt to the shape of the catheter to be retained.

In order to help fix the adjustable plate 54 with respect to the fixed plate 52 in use, ratchet teeth 62 may be provided on the adjustable plate 54 and a pawl 74 may be provided on the arm 72 that is secured to the fixed plate 52. It will be understood that the fixed plate 52 and the adjustable plate 54 may be fabricated from a suitable material, such as metal or plastic, that will have some resiliency or give. Preferably, the fixed plate 52 and the adjustable plate 54 are molded from a suitable plastic, such as polypropylene, nylon, polycarbonate or acrylonitrile butadiene styrene (ABS). The retention means can be molded integrally with the fixed plate 52 and the adjustable plate 54, respectively. Thus, the pawl 74 is constructed and arranged to have limited movement with respect to the ratchet teeth 62. When the pawl 74 is engaged between a pair of adjacent ratchet teeth 62, the adjustable plate 54 will be held in desired adjusted position with respect to the fixed plate 52. When the pawl 74 is released from the ratchet teeth 62, the adjustable plate 54 can be rotated with respect to the fixed plate 52. The pawl 74 cooperates with the ratchet teeth 62 to resist rotational movement of the adjustable plate 54 with respect to the fixed plate 52.

The multipurpose catheter securement device of FIG. 8 can be used for Foley catheters and for catheters with Luer locks.

Figure 9:
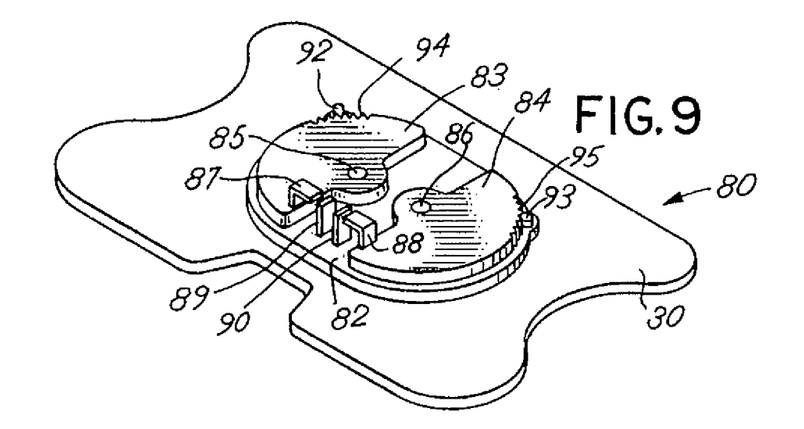
FIG. 9 shows a sixth embodiment of an adjustable catheter securement device embodying principles of the present invention, utilizing a fixed plate and two adjustable plates.

There is shown in FIG. 9 a further embodiment of the present invention which utilizes two rotational plates affixed to a fixed plate for accommodating various medical implements. The securement device 80 includes a base 30 that has an adhesive on at least a portion of the surface to be applied to the skin of a patient, a fixed plate 82 secured to the base 30 having a generally ovular shape and a pair of adjustable plates 83, 84 rotationally secured to the fixed plate 82 by pivot pins 85, 86. An angle bracket 87 is affixed to the adjustable plate 83 and an angle bracket 88 is affixed to the adjustable plate 84. Secured to the fixed plate are posts or tabs 89, 90. The tab 89 cooperates with the bracket 87 and the tab 90 cooperates with the bracket 88. The bracket 87 and tab 89 provide retention means for connecting to the leg or portion of a medical implement, such as a catheter and the bracket 88 and tab 90 provide like retention means.

In order to help fix or retain the adjustable plate 83 in a selected position with respect to the fixed plate 82 in use, ratchet teeth 94 may be provided on the adjustable plate 83 and a pawl 92 may be provided on the fixed plate 82. In order to help fix or retain the adjustable plate 84 in a selected position with respect to the fixed plate 82 in use, ratchet teeth 95 may be provided on the periphery of the adjustable plate 84 and a pawl 93 may be provided on the fixed plate 82. The pawl 92 is constructed and arranged to have limited flex movement with respect to the ratchet teeth 94. When the pawl 92 is released from the ratchet teeth 94, the adjustable plate 83 can be rotated with respect to the fixed plate 82 about pivot pin 85. When the pawl 92 is engaged between a pair of adjacent ratchet teeth 94, the position of the adjustable plate 83 is fixed with respect to the fixed plate 82. The pawl 92 cooperates with the ratchet teeth 94 to resist rotational movement of the adjustable plate 83 with respect to the fixed plate 82. Similarly, the pawl 93 is constructed and arranged to have limited movement with respect to the ratchet teeth 95. When the pawl 93 is released from the ratchet teeth 95, the adjustable plate 84 can be rotated with respect to the fixed plate 82 about pivot pin 86. When the pawl 93 is engaged in a valley between adjacent selected ratchet teeth 95, the position of the adjustable plate 84 is fixed with respect to the fixed plate 82. The pawl 93 cooperates with the ratchet teeth 95 to resist rotational movement of the adjustable plate 84 with respect to the fixed plate 82. Alternately, the ratchet teeth can be constructed and arranged with respect to the pawl to permit limited rotation of the plate with which the teeth are associated to move in one direction, but not the other. In other words, to function as a more conventional ratchet teeth and pawl.

It will be understood that the fixed plate 82 and the adjustable plates 83, 84 may be fabricated from a suitable material, such as metal or plastic, that will have some resiliency or give. Preferably, the fixed plate 82 and the adjustable plates 83, 84 are each molded from a suitable plastic, such as polypropylene, nylon, polycarbonate or acrylonitrile butadrene syrene (ABS). The tabs 89, 90 can be molded integrally with the fixed plate 82 and the brackets 87, 88 can be molded integrally with the adjustable plates 83, 84, respectively. The bracket 87 and tab 89 can be considered to be a retention means for retaining a catheter or like medical implement. The bracket 88 and the tab 90 can be similarly considered to be retention means.

The securement device of FIG. 9 can be used for Stat-Lock® Dialysis II equivalent and VDS2 devices.

Figure 10:
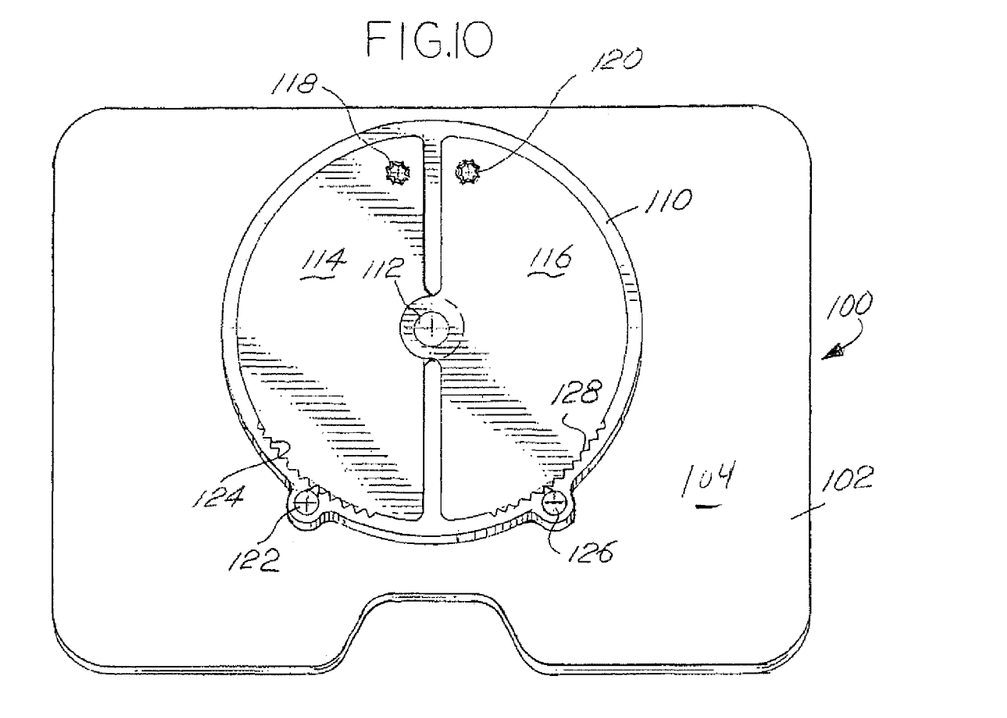
FIG. 10 is plan view of a seventh embodiment of the adjustable catheter securement device embodying principles of the present invention.
Figure 11:
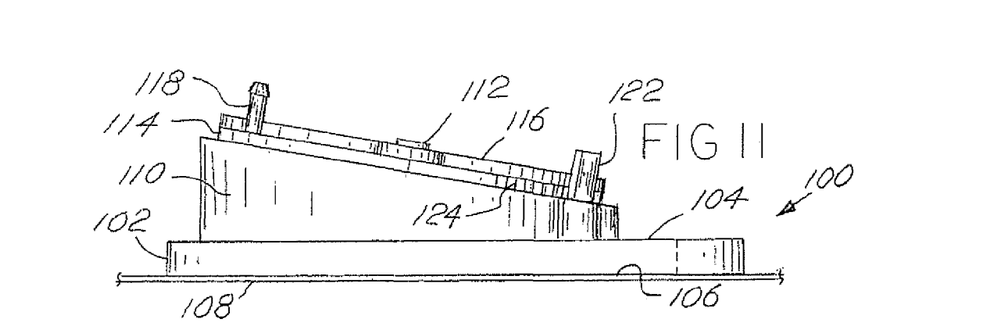
FIG. 11 is a left side view of adjustable catheter securement device of FIG. 10.
Figure 12:
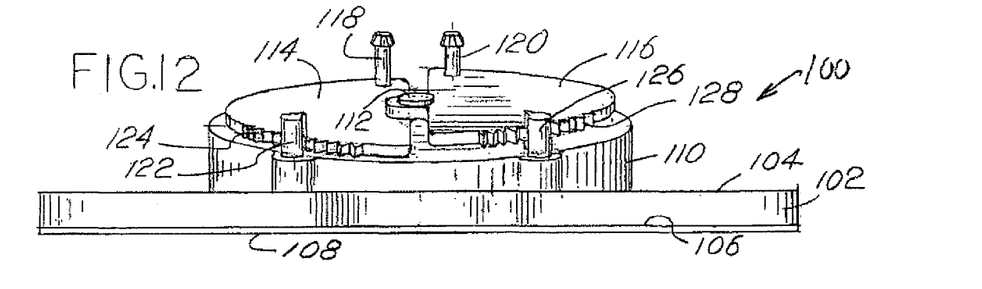
FIG. 12 is a front view of the adjustable catheter securement device of FIG. 10.

With reference to FIGS. 10-12, there is shown a securement device 100 having a flexible pad 102 with a top surface 104 and a bottom surface 106. At least a portion of the bottom surface 106 has adhesive 108 thereon for attaching the securement device 100 to the body of a patient. A base 110 is secured to the top surface 104 of the pad 102 of the securement device 100. Pivotally secured on the base 110 by a pivot pin 112 are a pair of adjustable plates 114, 116. The pivot pin 112 can be in the form of a short shaft or rod secured to the base 110 and having a slotted head thereon for receiving and retaining the arms 114, 116. The adjustable plate 114 has a post 118 projecting upwardly from the top surface thereof. The adjustable plate 116 has a post 120 projecting upwardly from the top surface thereof. The posts 118 and 120 can be considered to be retention means for engaging with and retaining a catheter.

Pawl and ratchet means are provided to permit adjustment of the plates 114 and 116 with respect to one another and to fix or retain the adjustable plates 114, 116 in their selected adjusted positions. A pawl 122 on the base 110 cooperates with ratchet teeth 124 on a circumferential portion of the plate 114 to permit limited movement of the plate 114 in one direction. A pawl 126 on the base 110 cooperates with ratchet teeth 128 on a circumferential portion of the plate 116 to permit limited movement of the plate 116 in one direction. Thus, the plates 114 and 116 can be rotatably adjusted to appropriately adjust the position of the posts 118 and 120 with respect to one another to accommodate various catheters.

The top surface of the base 110 can be arranged to form an acute angle with respect to the top surface of the pad 102. The angle between the top surface of the base 110 and the top surface of the pad 104 is about 30 degrees or less and preferably on the order of 10-15 degrees. With a catheter in place on the securement device 100, the catheter needle will be retained at an angle which is desirable for patient comfort.

Figure 13:
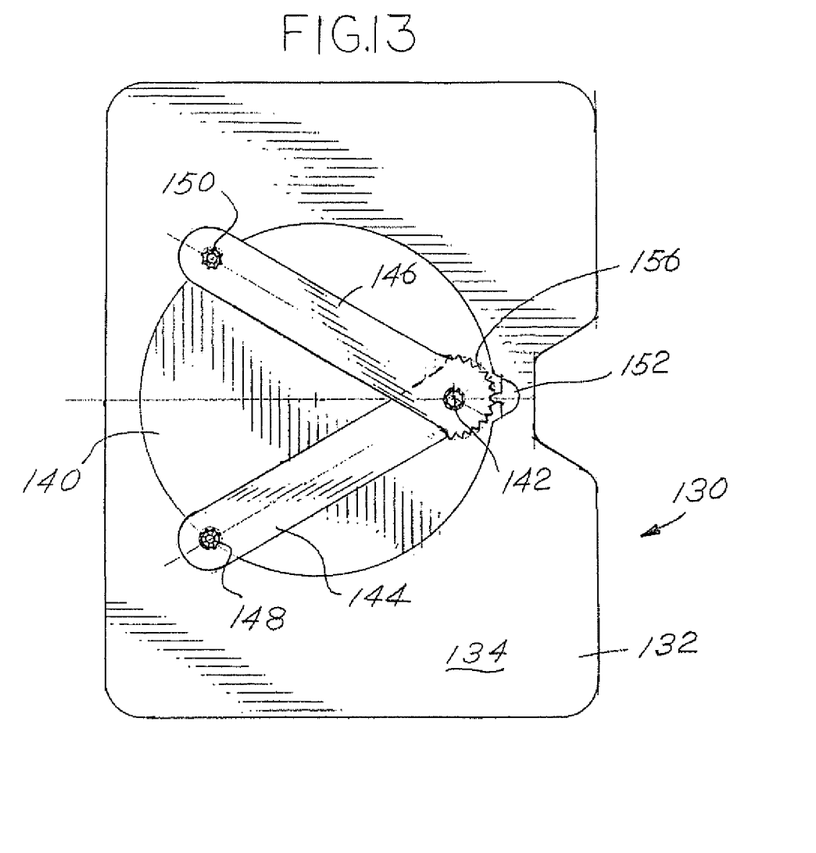
FIG. 13 is a plan view of an eighth embodiment of adjustable catheter securement device embodying principles of the present invention.
Figure 14:
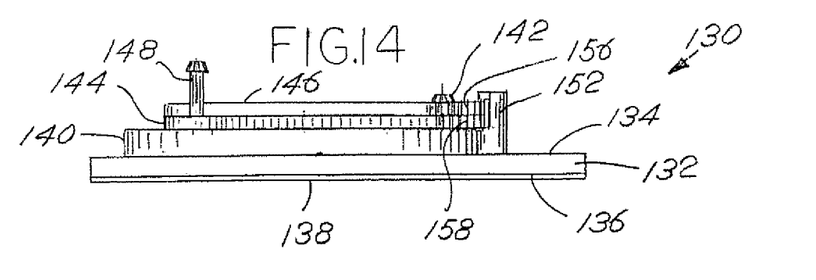
FIG. 14 is a front view of the adjustable catheter securement device of FIG. 13.

Referring to FIGS. 13 and 14 there is shown a securement device 130 having a flexible pad 132 with a top surface 134 and a bottom surface 136. At least a portion of the bottom surface 136 has adhesive 138 thereon for attaching the securement device 130 to the body of a patient. A base 140 is secured to the top surface 134 of the pad 132 of the securement device 130. Pivotally secured on the base 140 by a pivot pin 142 are a pair of adjustable arms 144, 146. The pivot pin 142 can be in the form of a short shaft or rod secured to the base 140 and having a slotted head thereon for receiving and retaining the arms 144, 146. The arm 144 has a post 148 projecting upwardly from the top surface thereof. The arm 146 has a post 150 projecting upwardly from the top surface thereof. The posts 148 and 150 can be considered to be retention means for engaging with and retaining a catheter. The top of the posts 148, 150 can be in various shapes, for example, a button or pyramid or Christmas tree ball structure and the top can be slotted, if desired. The sides of the posts 148, 150 can be textured if needed for a particular application. If desired, the posts 148 and 150 can be adjusted on the arms 144, 146. For example, the posts 148, 150 could be fixed to the arms radially inwardly from the positions shown in FIG. 13. The securement device 130 can readily be adapted to retain a broad scope of catheters of different sizes and shapes.

Pawl and ratchet means are provided on the securement device 130 of FIG. 13 to permit adjustment of the arms 144 and 146 with respect to one another and to fix or retain the adjustable arms in their selected adjusted positions. A pawl 152 on the base 140 cooperates with ratchet teeth 156 on a circumferential portion of the arm 144 and ratchet teeth 158 on a circumferential portion on the end of arm 146 to permit limited movement of the arms 144, 146 with respect to one another. Thus, the arms 144 and 146 can be rotatably adjusted to appropriately adjust the position of the posts 148 and 150 with respect to one another to accommodate various catheters.

Preferably, the base 100 and the plates 114 and 116 of the embodiment of FIGS. 10-12 and the base 140 and adjustable arms 144, 146 of the embodiment of FIGS. 13 and 14 are each molded from a suitable plastic, such as polypropylene, nylon, polycarbonate or acrylonitrile butadiene syrene (ABS). The posts 118 and 120 can be molded integrally with the plates 114, 116, respectively, and the posts 148, 150, respectively, can be molded integrally with the adjustable arms 144, 146, respectively. The pivot pin 112 can be a separate member secured to the base 110 or it can be molded integrally with base 110. Likewise, pivot pin 142 can be molded integrally with the base 140 or it can be a separate member.

While I have shown presently preferred embodiments of the present invention, it will be understood by persons skilled in the art that the invention may be otherwise embodied within the scope of the following claims.

The invention claimed is:

1. A device for securing a medical implement to a body of a patient, the device comprising:
   a pad having a bottom surface, at least a portion of the bottom surface having an adhesive thereon for attaching the securement device to the body of the patient;
   a fixed plate coupled to the pad, the fixed plate having a top surface wherein a portion of the top surface is planar;
   a first adjustable plate rotationally coupled to the fixed plate with an axis of rotation perpendicular to the planar portion of the top surface of the fixed plate;
   at least one tab coupled to the fixed plate and the first adjustable plate, respectively, wherein the at least one tab is configured to cooperatively secure a first portion of the medical implement when the first adjustable plate rotates relative to the fixed plate such that the at least one tab coupled to the adjustable plate is brought into proximity with the at least one tab coupled to the fixed plate;
   a first plurality of ratchet teeth coupled to the first adjustable plate; and
   a first pawl coupled to the fixed plate, the first pawl configured to engage the first plurality of ratchet teeth to resist rotational movement of the first adjustable plate with respect to the fixed plate.

2. The securement device of claim 1, wherein a first tab is an angle bracket and a second tab is a flat tab, wherein the first and second tabs are configured to cooperatively form a passage when the first tab is brought into proximity with the second tab.

3. The securement device of claim 1, wherein the planar portion of the top surface of the fixed plate is at an angle in the range of 0-15 degrees relative to the bottom surface of the pad.

4. The securement device of claim 1, further comprising:
   a second adjustable plate rotationally coupled to the fixed plate with an axis of rotation perpendicular to the top surface of the fixed plate;
   at least one tab coupled to the second adjustable plate, wherein the at least one tab coupled to the second adjustable plate and the at least one tab coupled to the fixed plate are configured to cooperatively secure a second portion of the medical implement when the second adjustable plate rotates relative to the fixed plate such that the at least one tab coupled to the second adjustable plate is brought into proximity with the at least one tab coupled to the fixed plate;
   a second plurality of ratchet teeth coupled to the second adjustable plate; and
   a second pawl coupled to the fixed plate, the second pawl configured to engage the second plurality of ratchet teeth to resist rotational movement of the second adjustable plate with respect to the fixed plate.

5. The securement device of claim 4, wherein the fixed plate comprises at least two tabs.

6. The securement device of claim 4, wherein:
one of the at least one tabs coupled to the first adjustable plate is an angle bracket;
one of the at least one tabs coupled to the second adjustable plate is an angle bracket; and
one of the at least one tabs coupled to the fixed plate is a flat tab;
wherein the angle brackets are configured to cooperatively form a passage when the first and second adjustable plates are brought into proximity with the at least one tab coupled to the fixed plate.

7. The securement device of claim 4, wherein the first and second adjustable plates are rotationally coupled to the fixed plate by two pivot pins.

8. The securement device of claim 4, wherein the first and second adjustable plates are rotationally coupled to the fixed plate by a single pivot pin.

9. A method for securing a medical implement to the body of a patient using the device of claim 1, comprising the steps of:
adhering a pad having a fixed plate and an adjustable plate to the body of a patient;
disposing a medical implement on a top surface of the device; and
rotating the adjustable plate relative to the fixed plate such that the at least one tab coupled to the adjustable plate is brought into proximity with the at least one tab coupled to the fixed plate,
wherein a portion of the medical implement is retained within a passage formed by the at least one tab coupled to the adjustable plate and at least one tab coupled to the fixed plate.

10. A system for securing a medical implement to a body of a patient, the system comprising:
the medical implement;
a pad having a bottom surface, at least a portion of the bottom surface having an adhesive thereon for attaching the medical implement to the body of the patient;
a fixed plate fixedly coupled to the pad, the fixed plate having a top surface wherein a portion of the top surface is planar;
a first adjustable plate rotationally coupled to the fixed plate with an axis of rotation perpendicular to the planar portion of the top surface of the fixed plate;
at least one tab coupled to the fixed plate and the first adjustable plate, respectively, wherein the tabs are configured to cooperatively secure a first portion of the medical implement when the first adjustable plate rotates relative to the fixed plate such that the at least one tab coupled to the adjustable plate is brought into proximity with the at least one tab coupled to the fixed plate;
a first plurality of ratchet teeth coupled to the first adjustable plate; and
a first pawl coupled to the fixed plate, the first pawl configured to engage the first plurality of ratchet teeth to resist rotational movement of the first adjustable plate with respect to the fixed plate.

11. The system of claim 10, wherein the medical instrument is a catheter.

\* \* \* \* \*